United States Patent [19]

Xu et al.

[11] Patent Number: 5,475,234
[45] Date of Patent: Dec. 12, 1995

[54] APPARATUS AND METHOD FOR MEASURING CONCENTRATIONS OF COMPONENTS USING PULSED LIGHT OF DIFFERENT WAVELENGTHS AND PERFORMING A TIME RESOLVED MEASUREMENT

[75] Inventors: Kexin Xu; Yutaka Yamasaki; Harumi Uenoyama; Takeshi Sakura, all of Kyoto, Japan

[73] Assignee: Kyoto Daiichi Kagaku Co., Ltd., Kyoto, Japan

[21] Appl. No.: 280,811

[22] Filed: Jul. 26, 1994

[30] Foreign Application Priority Data

Jul. 30, 1993 [JP] Japan .................................. 5-189900

[51] Int. Cl.⁶ .......................... G01N 15/06; G01N 21/49; G01N 21/85
[52] U.S. Cl. ................................ 250/573; 356/338
[58] Field of Search .................... 250/573, 574, 250/575; 356/338, 436

[56] References Cited

U.S. PATENT DOCUMENTS

| | | | |
|---|---|---|---|
| 2,610,541 | 9/1952 | Rowland, Jr. .......................... | 88/14 |
| 2,854,585 | 9/1958 | Simmons ................................ | 250/209 |
| 4,544,274 | 10/1985 | Cremers et al. ...................... | 356/436 |
| 5,070,246 | 12/1991 | Durham et al. ....................... | 250/373 |
| 5,119,815 | 6/1992 | Chance . | |
| 5,353,790 | 10/1994 | Jacques et al. ...................... | 128/633 |

OTHER PUBLICATIONS

Time Resolved Spectroscopy and Imaging of Tissues, 1 Dec. 1991, "Noninvasive Measurement . . . ," McCormick et al., pp. 294–302.

Proceedings of IEEE, vol. 80, No. 6, 1 Jun. 1992, pp. 918–930, Wilson et al., "Time Dependent Optical Spectroscopy . . . ".

Physics in Medicine and Biology, vol. 33, No. 12, 1 Dec. 1988, pp. 1433–1442, Delpy et al., "Estimation of Optical . . . ".

Applied Optics (1 Nov. 1991), vol. 30, No. 31, pp. 4515–4520.

J. Biochem. (1991), vol. 109, No. 3, p. 455–461.

Primary Examiner—David C. Nelms
Assistant Examiner—Stephen Calogero
Attorney, Agent, or Firm—Birch, Stewart, Kolasch & Birch

[57] ABSTRACT

An apparatus and method for measuring component concentrations which enables accurate measurement of concentrations of component within an object in a non-destructive, non-invasive, and bloodless procedure. The apparatus comprises a light irradiator 1 for projecting pulse laser of different wavelengths toward an object 12 by means of a variable wavelength laser generating unit 11, a photodetector 2 for performing a time resolved measurement of the quantity of transmitted light from the object which is subject to changes with lapse of time after the generation of the pulse laser, and an arithmetic unit 3 for calculating concentrations of components in the object 12 and outputting the calculation result such that the relationship between time lapse and measured quantity of light is converted into a relationship between an optical path length representing the distance of light travel within the object 12 and a change in the measured quantity of light relative to a change in unit concentration so that the optical path length and the quantity of light which is measured when the change in the quantity of light is at a peak are stored in memory for each wavelength, the quantity of light being used as a basis for the calculation.

7 Claims, 6 Drawing Sheets

APPARATUS AND METHOD FOR MEASURING CONCENTRATIONS OF COMPONENTS USING PULSED LIGHT OF DIFFERENT WAVELENGTHS AND PERFORMING A TIME RESOLVED MEASUREMENT

BACKGROUND OF THE INVENTION

1. Field of the Invention

The present invention relates to an apparatus and method for measuring concentrations of components which are suitable for use in carrying out non-destructive measurements and/or non-invasive, bloodless measurements.

2. Description of the Prior Art

Conventionally, in the fields of biology and medicine, a near infrared CT (computed tomography) has been known which enables a non-invasive, bloodless examination of an object. This technique utilizes the so-called time of flight method for near infrared rays in scattering optical system. For example, in the case of the near infrared CT, a pulse laser is irradiated toward the object from one side thereof for time-resolved measurement of quantity of light passing through the object which change with lapse of time, data for the changing quantity of light being disregarded except the data for the quantity of light which has passed through the object for an initial very short time period. An image of the interior of the object is formed on the basis of the data for the quantity of light obtained during the initial short time. In other words, the light which has reached the photoreceptor in the initial short time are considered as having passed through the interior of the object along the shortest possible optical path and only data for that quantity of light is used to obtain a clear and sharp image.

In the conventional near infrared CT, only an initial portion of the transmitted light varying with time lapse is utilized to obtain information on the interior of the object. For the purpose of measuring a concentration of a component in the object, however, it is not necessarily suitable to adopt the same concept as that of the near infrared CT.

In order to accurately determine a concentration of a component, it is necessary to increase the measurement accuracy of a measuring system, and for this purpose it is necessary to enhance the S/N ratio of the measuring system.

SUMMARY OF THE INVENTION

The present invention is directed to meeting the foregoing needs, and accordingly it is an object of the invention to provide an apparatus and method for measuring concentrations of components which enables accurate measurement of component concentrations within an object in a non-destructive, non-invasive, and bloodless procedure.

In order to accomplish the above object, according to a first aspect of the invention, there is provided an apparatus for measuring concentrations of components comprising a light irradiator for projecting pulse light of different wavelengths toward an object, a photodetector for performing a time resolved measurement of the quantity of light with respect to at least one of reflected light and transmitted light from the object which is subject to changes with lapse of time after the generation of the pulse light, and an arithmetic unit for calculating the concentrations of the components in the object and outputting the calculation result such that the relationship between time lapse and measured quantity of light is converted into a relationship between an optical path length representing the distance of light travel within the object and a change in the measured quantity of light relative to a change in unit concentration so that the optical path length and the quantity of light which is measured when the change in the quantity of light is at a peak are stored in memory to enable selection of an optimum optical path length for each wavelength, with the quantity of light for the optimum optical path length being used as a basis for the calculation.

According to a second aspect of the invention, the light irradiator comprises a laser generating unit capable of generating pulse laser of different wavelengths.

According to a third aspect of the invention, the laser generating unit is a variable wavelength laser generating unit.

According to a fourth aspect of the invention, there is provided a method for measuring concentrations of components which comprises projecting pulse light of a selected wavelength from a light irradiator toward an object; causing a photodetector to perform a time resolved measurement of the quantity of light with respect to at least one of reflected light and transmitted light from the object which is subject to changes with lapse of time after the generation of the pulse light; storing the measured data in an arithmetic unit; and repeating the foregoing steps for different wavelengths of pulse light in such a manner that the arithmetic unit converts the relationship between time lapse and measured quantity of light into a relationship between an optical path length representing the distance of light travel within the object and a change in the measured quantity of light relative to the change in unit concentration so that the optical path length and the quantity of light which is measured when the change in the quantity of light is at a peak are stored in memory for each wavelength to enable selection of an optimum optical path length for each wavelength, whereby the concentrations of the components in the object is calculated on the basis of the quantity of light for the optimum optical path length, the calculated result being then output.

According to a fifth aspect of the invention, there is provided a method for measuring concentrations of components which comprises the steps of:

(i) generating pulsed light of a selected wavelength from a light irradiator and causing a photodetector to perform a time resolved measurement of the quantity of received light $I_R$ from an object which serves as a reference and is subject to changes with lapse of time t;

(ii) projecting pulse light of the selected wavelength from the light irradiator toward the object and causing the photodetector to perform a time resolved measurement of the quantity of transmitted light $I_t$ from the object which is subject to changes with lapse of time t;

(iii) with respect to the measured quantity of received light $I_R(L)$ and measured quantity of transmitted light $I_t(L)$ which are subject to changes with an optical path length L corresponding to lapse of time t, selecting a reference quantity of received light $I_R(L_o)$ and a reference quantity of transmitted light $I_t(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation $L=Ct$ which expresses the relationship between optical path length $L$ and lapse of time $t$;

(vii) calculating the quantity of transmitted light $I_{tp}(t_p)$ from the object for a certain wavelength $\lambda$ at optimum lapse of time $t_p$;

(viii) calculating, on the basis of the quantity of received light $I_{RP}$ and quantity of transmitted light $I_{tp}$ at the optimum lapse of time and from equation $A=\log_{10}(I_R/I_t)$ for absorbance $A$, an absorbance $A_p$ corresponding to $I_{RP}$ and $I_{tp}$; and (ix) repeating the foregoing steps for plural wavelengths, whereby on the basis of respective calculated absorbances are carried out multivariate analysis to calculate the concentrations of the components in the object, the calculated results being then output.

According to a sixth aspect of the invention, there is provided a method for measuring concentration of components which comprises the steps of:

(i) generating pulse light of a selected wavelength from a light irradiator and causing a photodetector to perform a time resolved measurement of the quantity of received light $I_R$ from an object which serves as a reference and is subject to changes with lapse of time $t$;

(ii) projecting pulse light of the selected wavelength from the light irradiator toward the object and causing the photodetector to perform a time resolved measurement of the quantity of reflected light $I_r$ from the object which is subject to changes with lapse of time $t$;

(iii) with respect to the measured quantity of received light $I_R(L)$ and measured quantity of reflected light $I_r(L)$ which are subject to changes with an optical path length $L$ corresponding to lapse of time $t$, selecting a reference quantity of received light $I_R(L_o)$ and a reference quantity of reflected light $I_r(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation $L=Ct$ which expresses the relationship between optical path length $L$ and lapse of time $t$;

(vii) calculating the quantity of reflected light $I_{rp}(t_p)$ from the object for a certain wavelength $\lambda$ at optimum lapse of time $t_p$;

(viii) calculating, on the basis of the quantity of received light $I_{RP}$ and quantity of reflected light $I_{rp}$ at the optimum lapse of time and from equation $A=\log_{10}(I_R/I_r)$ for absorbance $A$, an absorbance $A_p$ corresponding to $I_{RP}$ and $I_{rp}$; and (ix) repeating the foregoing steps for plural wavelengths, whereby on the basis of respective calculated absorbances are carried out multivariate analysis to calculate the concentrations of the components in the object, the calculated results being then output.

According to a seventh aspect of the invention, there is provided a method for measuring concentrations of components which comprises the steps of:

(i) generating pulse light of a selected wavelength from a light irradiator and causing a photodetector to perform a time resolved measurement of the quantity of received light $I_R$ from an object which serves as a reference and is subject to changes with lapse of time $t$;

(ii) projecting pulse light of the selected wavelength from the light irradiator toward the object and causing the photodetector to perform a time resolved measurement of the quantity of transmitted light $I_t$ and quantity of reflected light $I_r$ from the object which are subject to changes with lapse of time $t$;

(iii) with respect to the measured quantity of received light $I_R(L)$, measured quantity of transmitted light $I_t(L)$ and measured quantity of reflected light $I_r(L)$ which are subject to changes with an optical path length $L$ corresponding to lapse of time $t$, selecting a reference quantity of received light $I_R(L_o)$, a reference quantity of transmitted light $I_t(L_o)$, and a reference quantity of reflected light $I_r(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation $L=Ct$ which expresses the relationship between optical path length $L$ and lapse of time $t$;

(vii) calculating the quantity of transmitted light $I_{tp}(t_p)$ and quantity of reflected light $I_{rp}(t_p)$ from the object for a certain wavelength $\lambda$ at optimum lapse of time $t_p$;

(viii) calculating, on the basis of the quantity of received light $I_{RP}$, quantity of transmitted light $I_t$, and quantity of reflected light $I_{rp}$ at the optimum lapse of time and from equation $A=\log_{10}(I_R/I_r)$ for absorbance $A$, an absorbance $A_p$ corresponding to $I_R p$, $I_t p$ and $I$; and (ix) repeating the foregoing steps for plural wavelengths, whereby on the basis of respective calculated absorbances are carried out multivariate analysis to calculate the concentrations of the components in the object, the calculated results being then output.

By arranging for the foregoing steps being carried out it is possible to determine the concentration of the component in the object from at least one of the quantity of reflected light and the quantity of transmitted light under conditions that can provide a maximum S/N ratio in a non-destructive, non-invasive and bloodless manner.

DETAILED DESCRIPTION OF THE PREFERRED EMBODIMENTS

One embodiment of the invention will now be described with reference to the accompanying drawings.

Figure 1:
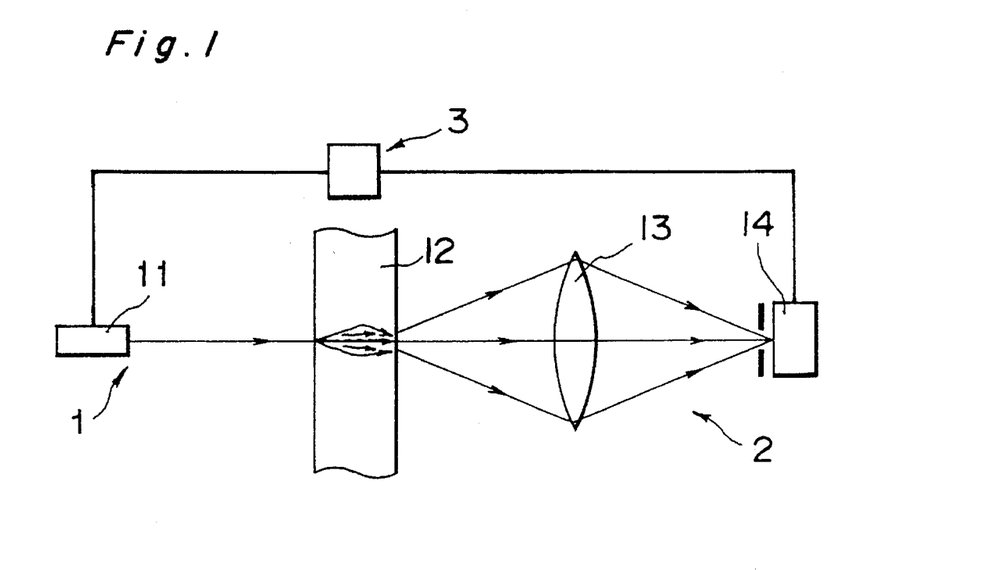
FIG. 1 is a schematic diagram showing an apparatus for measuring concentrations of components according to a first embodiment of one aspect of the present invention, to which methods for measuring concentrations of components of another aspect of the present invention are applied.
Figure 2:
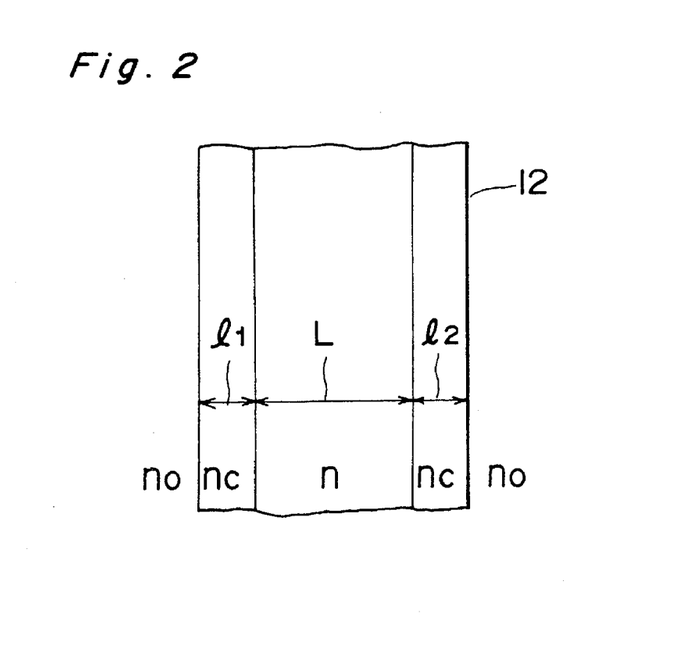
FIG. 2 is a diagram optically schematically showing a portion of the object shown in FIG. 1.

FIGS. 1 and 2 illustrate an apparatus for measuring concentrations of components, according to a first embodiment of one aspect of the present invention, to which methods for measuring concentrations of components, of another aspect of the present invention are applied. The apparatus comprises a light irradiator 1, a photodetector 2, and an arithmetic unit 3.

The light irradiator 1 comprises a variable wavelength pulse laser generating unit 11 which is capable of changing the wavelength of laser projected toward an object 12.

The photodetector 2 includes a lens 13 and a quantity of light sensing means 14, and is operative to measure the quantity of transmitted light through the object 12 which is subject to changes with lapse of time after generation of the pulse laser. It is noted in this connection that the lens 13 has a function to converge transmitted light from the object 12 toward a photodetector of the quantity of light sensing means 14.

The arithmetic unit 3 converts the relationship between time lapse and measured quantity of light into a relationship between an optical path length representing the distance of light travel in the process of light scattering within the object 12 and a change in the measured quantity of light relative to a change in unit concentration, and stores in memory, for each respective wavelength, a particular optical path length in which a peak in such changes in measured quantity of light occurs. On the basis of such a peak value and such a particular optical path length for each wavelength, calculation is made of the concentration of a component in the object 12, such as, for example, glucose, haemoglobin, protein, bilirubin, and saccharide.

The arithmetic unit 3 is connected to the variable wavelength pulse laser generating unit 11, and this enables measured quantity of transmitted light and the wavelength of transmitted light to be associated with each other.

Nextly, methods for measuring concentrations of components according to the fourth and fifth aspects of the present invention will be explained which are applied to the above described first embodiment.

Initially, in the absence of the object 12 in FIG. 1, pulse laser of a selected wavelength, preferably of near infrared region, are projected from the variable wavelength pulse laser generating unit 11 which constitutes the light irradiator 1, to provide a reference quantity of received light $I_R$ from the object which is subject to changes with lapse of time t after generation of the pulse laser. The photodetector 2 performs a time resolved measurement of the reference quantity of received light $I_R$.

Then, in a state that the apparatus is disposed for the object 12 as shown in FIG. 1, pulse laser of the same wavelength as the initially generated pulse laser are projected from the variable wavelength pulse laser generating unit 11 toward the object 12, and time resolved measurement is carried out by the photodetector 2 with respect to the quantity of transmitted light $I_t$ from the object 12 which is subject to changes with lapse of time t.

The data obtained through the time resolved measurement is stored in memory within the arithmetic unit 3.

The above described steps are repeated for different wavelengths of pulse laser.

At the arithmetic unit 3, the relationship between lapse of time and measured quantity of light is converted into a relationship between an optical path length or the distance of light travel within the object 12 and a change in the measured quantity of light relative to a change in unit concentration, and a particular optical path length and a particular quantity of light which are coincident with a peak in such changes in measured quantity of light are stored in memory for each wavelength. The concentration of a component within the object is calculated on the basis of such particular optical path length and quantity of light for each wavelength and from equations which will be described hereinafter. The calculated results are output.

In the present example, the concentration of the component is calculated on the basis of the quantity of transmitted light from the object 12. Alternatively, the concentration of the component may be calculated from the quantity of reflected light from the object 12 as will be described hereinafter.

Figure 3:
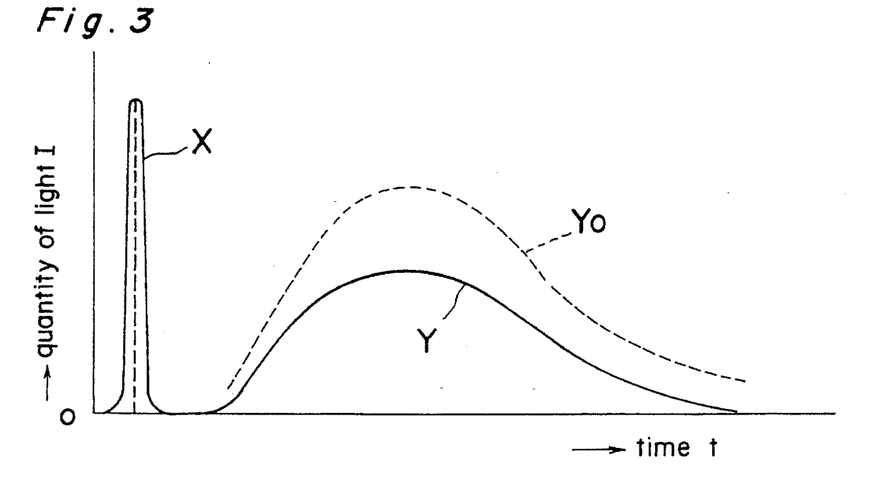
FIG. 3 is a chart showing the quantity of light of pulse laser of a single wavelength (curve X) generated from a light irradiator, the quantity of transmitted light through the object (curve Y), and the quantity of transmitted light through the object without light absorption (curve $Y_o$) in relation to lapse of time.

FIG. 3 shows the quantity of light of pulse laser of a single wavelength (curve X) generated from the light irradiator 1, and the quantity of transmitted light (curve Y, $Y_o$) in relation to lapse of time t. Curve Y represents the quantity of transmitted light from the object 12, and curve $Y_o$ represents the quantity of received light without absorption. The quantity of transmitted light is subject to change with lapse of time after generation of the pulse laser. The lapse of time corresponds to the distance of light travel in the process of laser scattering, that is, the optical path length. Namely, value obtained by multiplying time of abscissa by light velocity c gives optical path length.

The relationship shown in FIG. 3 is measured for different wavelengths.

For each respective wavelength, there exists an optical path length which gives a maximum change $dI_t$ in quantity of transmitted light $I_t$.

Nextly, the theory used as the basis for calculation of component concentration at the arithmetic unit 3 will be explained.

The quantity of light that has passed through the object is calculated as follows according to the LAMBERT-BEER's equation:

$$I_t = I_o \exp(-\Sigma \alpha_i C_i L) \quad (1)$$
$$= I_o \gamma$$

where $\gamma = \exp(-\Sigma \alpha_j C_j L)$ $I_o$: quantity of incident light, $I_t$: quantity of transmitted light, $\alpha_i$: extinction coefficient of i component of the object, $\alpha_c$: extinction coefficient of the object, (function of wavelength)

L: distance of light travel in the process of light scattering within the object (length of light path), $C_i$: concentration of i component of the object.

Here, quantity-of-light measurement sensitivity S relative to i component of the object is defined as follows:

$$S = dI_t/dC_j, \quad (2)$$

where $dI_t$: change in quantity of transmitted light $I_t$ based on change $dC_i$ in the concentration of i component $dC_i$: change in the concentration of i component From Equation (2), $$S = I_o d\gamma/dC_i \quad (3)$$
$$= I_o \gamma\{(-d\Sigma \alpha_i C_i L)/dC_i\}$$
$$= I_o \gamma\{\alpha_i - (\Sigma \alpha_i dC_i/dC_i)\}L$$
$$= I_o f L \gamma$$

where $f = \alpha_i - \Sigma \alpha_j (dC_j/dC_i)$

Since $\gamma$ and f are functions of wavelength $\lambda$, quantity-of-light measurement sensitivity is represented by $S_\lambda$. Accordingly, Equation (3) is rewritten as follows:

$$S_\lambda = I_o f \gamma L \quad (4)$$

$$dS_\lambda/dL = 0 \quad (5)$$

Therefore, $1 - \Sigma \alpha_{j\lambda} C_j L = 0$

Therefore, when $$L = 1/\Sigma \alpha_{j\lambda} C_j \text{ (Let L be } L_\lambda) \quad (6)$$

(6) quantity-of-light measurement sensitivity S reaches maximum. This maximum value is expressed by $S_{c\lambda max}$.

Absorbance A $(=\log_{10}(I_{p\lambda}/I_o)$ is rewritten as follows:

$A = \log_{10} e = 0.4343$

As stated above, with respect to light of a certain wavelength $\lambda$ there exists an optimum optical path length $L_{p\lambda}$ which enables maximum value $S_{\lambda max}$ of light quantity measurement sensitivity $S_\lambda$ to be obtained.

Specifically, optical path length $L_{p\lambda}$ is calculated from ratio of one to another quantity-of-light measurement sensitivity at different optical path lengths as follows:

$$S_{\lambda L} = I_o f \gamma L \quad (7)$$

Accordingly, quantity-of-light measurement sensitivity at reference optical path length $L_o$ is expressed by the following equation:

$$S_o = I_o f \gamma_o L_o \quad (8)$$

The ratio of $S_{\lambda L}$ to $S_{\lambda Lo}$ is represented by M.

$$M = S_{\lambda L}/S_{\lambda Lo} \quad (9)$$
$$= \gamma L/\gamma_o L_o$$
$$= k \gamma_o^{(k-1)}$$

where $$k = L/L_o \quad (10)$$

$dM/dt = 0$

From the above and Equation (1):

$$k(=L/L_o) = -1/\log_{10} \gamma_o \text{ (Let k be } k_p) \quad (11)$$

In this case, M reaches maximum and accordingly $S_\lambda$ reaches maximum. The value of M in this case is expressed by $M_{max}$.

In other words, optimum optical path length $L_{p\lambda}$ at which quantity-of-light measurement sensitivity $S_\lambda$ reaches maximum is calculated. This optimum optical path length $L_{p\lambda}$ is determined for each wavelength.

It is noted that $\gamma_o$ is a measurable quantity and constant.

Absorbance $A_{80}$ is calculated on the basis of the optimum optical path length $L_{p\lambda}$ and the corresponding quantity of transmitted light, and the concentration of i component of the object 12 is calculated by multivariate analysis.

In the case of calculating the concentration of the component in the object 12 by measuring the quantity of reflected light $I_r$ from the object 12, the same theory as above described is applicable simply by replacing quantity of transmitted light $I_t$ by quantity of reflected light $I_r$. The same is true with the case of measuring both quantity of transmitted light and quantity of reflected light to calculate the concentration of the component from the measured values of the both.

In this way, according to the above described arrangement of the apparatus, from measurement data representing a larger S/N ratio at optimum wavelength and optimum optical path length L which enable maximum quantity-of-light measurement sensitivity to be obtained, the concentration of i component in the object 12 is calculated at the arithmetic unit 4 and is output therefrom. Therefore, by employing the apparatus it is possible to calculate the concentration of a component in the object 12 with high accuracy. In particular, the apparatus is suitable for measuring concentrations of components in case where there is no much difference between different objects in the concentration of a particular component.

Figure 4:
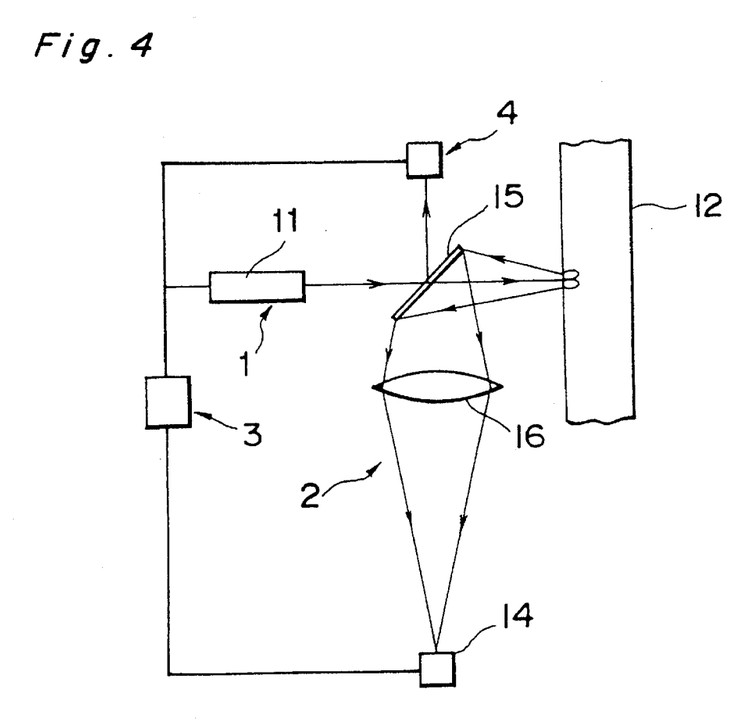
FIG. 4 is a schematic diagram showing an apparatus for measuring concentrations of components according to a second embodiment of one aspect of the present invention, to which methods for measuring concentrations of the components of another aspect of the present invention are applied.

FIG. 4 illustrates an apparatus for optically measuring concentrations of components according to a second embodiment of one aspect of the present invention, to which methods for optically measuring concentrations of components of another aspect of the present invention are applied. Parts identical with those of the apparatus shown in FIG. 1 are designated by like reference numerals, description being omitted with respect to those parts.

The apparatus of this embodiment comprises a light irradiator 1, a photodetector 2, an arithmetic unit 3, and a reference light receptor 4. The light irradiator 1 is identical with the light irradiator 1 in the first embodiment.

The photodetector 2 has, in addition to the quantity of light sensing means 14, a beam splitter 15 and a lens 16. The beam splitter 15 is operative to split a laser beam from the variable wavelength pulse laser generating unit 11 into two beams perpendicular to each other, that is, one travelling in a straightforward direction and the other travelling toward the reference light receptor 4. The beam splitter 15 also functions to reflect scattered light from the object 12 toward the lens 16. Light incident on the lens 16 are converged onto the quantity of light sensing means 14.

Figure 5:
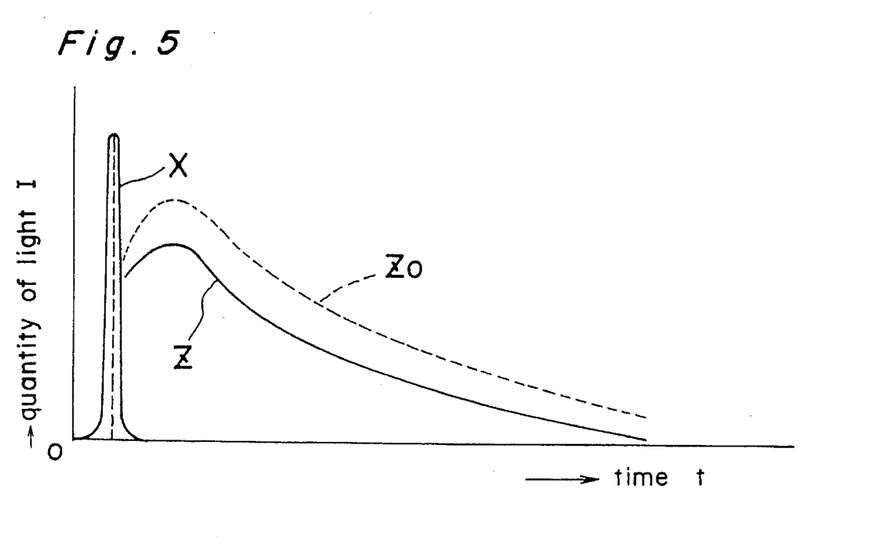
FIG. 5 is a chart showing the quantity of light of pulse laser of a single wavelength (curve X) generated from the light irradiator, the quantity of reflected light from the object (curve Z), and the quantity of reflected light through the object without light absorption (curve $Z_o$) in relation to lapse of time.

FIG. 5 shows the relationship between the quantity of light of pulse laser of a single wavelength (curve X) generated from the illuminating unit 1 and also the quantity of reflected light from the object 12 (curve Z), on one hand, and lapse of time t, on the other.

Curve $Z_o$ represents the relationship between the quantity of received light in the absence of light absorbing material and time of lapse t, and is used as a curve for the quantity of reference light $I_o$ in the scattered light system.

The relations shown in FIG. 5 are measured for plural wavelengths.

By comparing changes in the quantity of reflected light shown in FIG. 5 with changes in the quantity of transmitted light shown in FIG. 3, it can be seen that in the FIG. 5 case, as a whole, the time taken by light to reach the photodetector 2 is shorter than that in the FIG. 3 case. In other words, the optical path length of reflected light used in measurement by the apparatus of the second embodiment is shorter than that of transmitted light used in measurement by the first embodiment apparatus.

The ratio of the quantity of reflected light measured at the photodetector 2 to the quantity of received light at the reference light receptor 4 is taken as a basis for correction of time variation with respect to generated laser, so that on the basis of the corrected quantity of received light the concentration of the component in the object 12 is calculated, the calculated result being then output from the arithmetic unit 3.

In the present invention, the provision of the reference light receptor 4 for correcting the measurement made by the photodetector 2 is not essential.

Figure 6A:
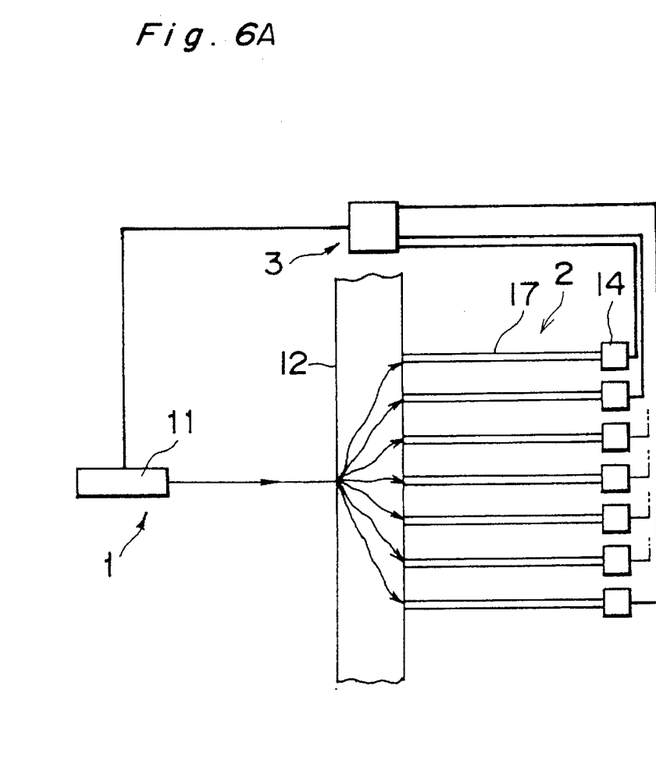
FIG. 6A is a schematic diagram showing an apparatus for measuring concentrations of components according to a third embodiment of one aspect of the present invention, to which methods for measuring concentrations of components another aspect of the present invention are applied.

FIG. 6 shows an apparatus for measuring concentrations of components according to the third embodiment of one aspect of the present invention, to which methods for measuring concentrations of components defined in claims 4 and 5 of another aspect of the present invention are applied. Parts identical with those of the foregoing embodiments are designated by like reference numerals, description being omitted with respect to those parts.

In the present embodiment, the photodetector 2 comprises a plurality of optical fiber elements 17 having a light receiving face held in abutment with one surface of the object 12 which is opposite from the light irradiator 1, and optical sensing means 14 attached to each of the optical fiber elements 17. The photodetector 2 is designed to conduct light rays which have passed through the object 12 while being scattered within the object 12, toward the optical sensing means 14 through the optical fiber elements 17.

Figure 6B:
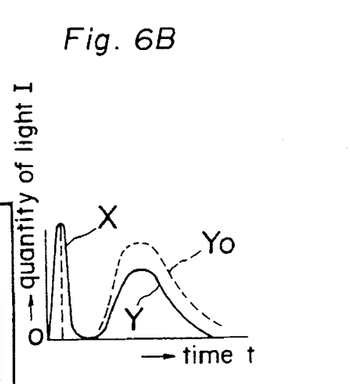
FIGS. 6B and 6C graphically illustrate quantities of transmitted light detected by the individual optical sensing means over time.
Figure 6C:
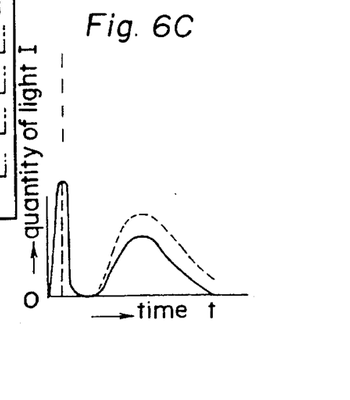

At the arithmetic unit 3, quantities of transmitted light detected by the individual optical sensing means 14 for each specified lapse of time are added up for each specified lapse of time, and the sum thereof is taken as the quantity of transmitted light for each specified optical path length. Thus, in the same manner as above described, the concentration of the component in the object 12 is calculated and the calculated result is output.

Figure 7:
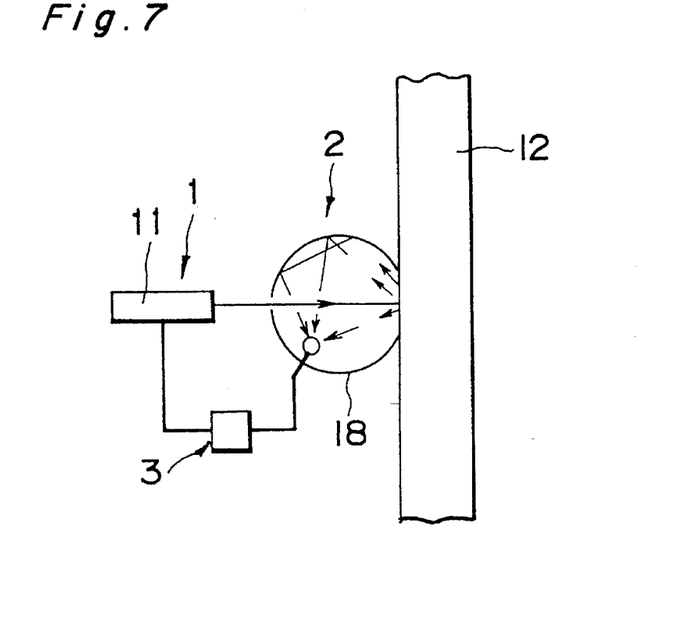
FIG. 7 is a schematic diagram showing an apparatus for measuring concentrations of components according to a fourth embodiment of one aspect of the present invention, to which methods for measuring concentrations of components of another aspect of the present invention are applied.

FIG. 7 shows an apparatus for measuring concentrations of components according to a fourth embodiment of one aspect of the present invention, to which methods for measuring concentrations of components of another aspect of the present invention are applied. Parts identical with those of the foregoing embodiments are designated by like reference numerals, description being omitted with respect to those parts.

In the present embodiment, the photodetector 2 has an integrating sphere 18 held in abutment with the surface of the object 12 which lies on the same side as the light irradiator 1, and is adapted to cause the scattered light reflected from the object 12 to be converged by the integrating sphere 18 for quantity of light detection so that, on the basis of the detected quantity of light and in the same manner as already described, the concentration of the component of the object 12 is calculated at the arithmetic unit 3, the calculated result being then output.

Figure 8:
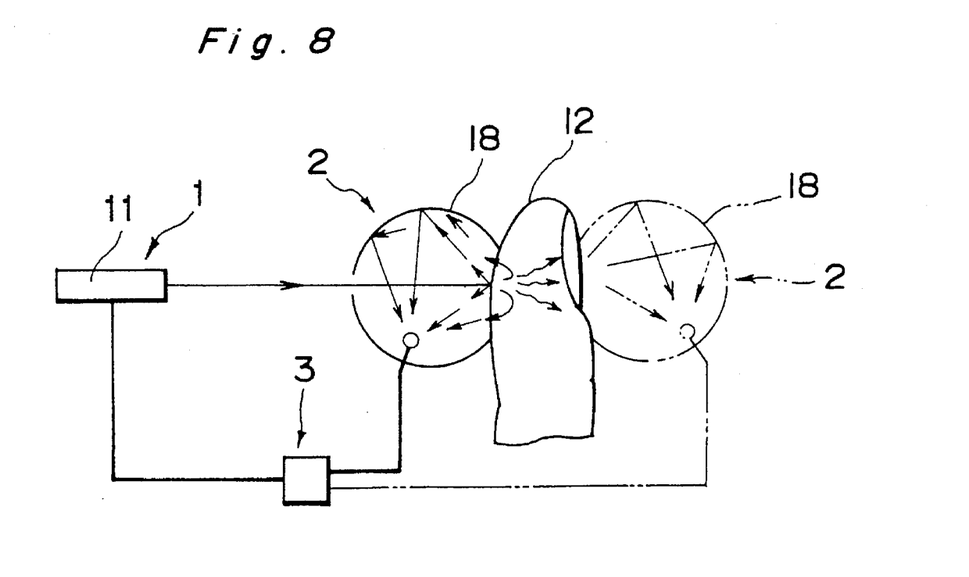
FIG. 8 is a schematic diagram showing an apparatus for measuring concentrations of components according to a fifth embodiment of one aspect of the present invention, to which methods for measuring concentrations of components of another aspect of the present invention are applied.

FIG. 8 shows an apparatus for measuring concentrations of components according to a fifth embodiment of one aspect of the present invention, to which methods for measuring concentrations of components of another aspect of the present invention are applied. This apparatus is identical with the above described fourth embodiment except that the object 12 is a human finger.

Figure 9:
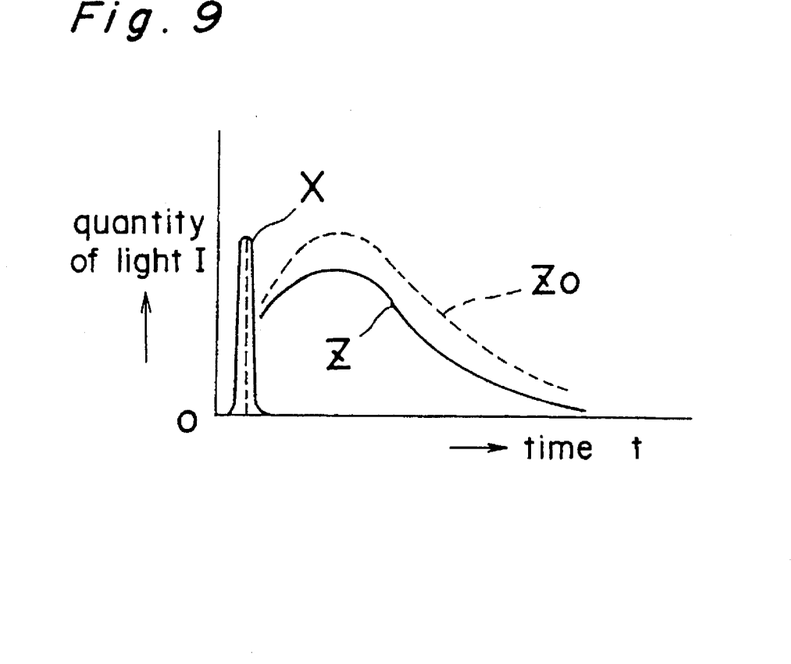
FIG. 9 is a chart showing the quantity of light of pulse laser of a single wavelength (curve X) generated from the light irradiator, the quantity of reflected light from the object (curve Z), and the quantity of reflected light from the object without light absorption (curve $Z_o$) in relation to lapse of time.

FIG. 9 shows the relationship between the quantity of pulse laser of a single wavelength (curve X) generated from the light irradiator 1 and also the quantity of reflected light from the object 12 which is detected by the integrating sphere 18 (curve Z), on one hand, and lapse of time t, on the other. Curve $Z_o$ represents the relationship between the quantity of received light in the absence of light absorption at the object 12 and time of lapse t, and is used as a curve for the quantity of reference light $I_o$ in the scattered light system.

It may be noted that, as shown by chain two-dashed lines in FIG. 8, the integrating sphere 18 may be held in abutment with the surface of the finger or the object 12 which is positioned opposite from the light irradiator 1, for detecting the quantity of light which has passed through the finger in the process of being scattered within the finger, so that on the basis of the detected quantity of light can be detected the concentration of the component in the object 12.

In the case of carrying out measurement of concentration with respect to a plurality of components, there may be cases where for one component, the optimum optical path length relative to a certain wavelength is shorter, whereas for another component, the optimum optical path length relative to the wavelength is longer. In such a case, it is necessary to measure respective quantities of light for the shorter optimum length of light path and for the longer optimum optical path length. In such a case, only with the integrating sphere 18 for measuring the quantity of transmitted light as shown by the chain two-dashed lines, the optical path length is excessively long and does not permit measurement of the quantity of transmitted light at the shorter optimum optical path length, so that measurement of the concentration of some component may be rendered impossible. Likewise, only with the integrating sphere 18 for measuring the quantity of reflected light as shown by the solid lines, the optical path length is excessively short and does not permit measurement of the quantity of reflected light at the longer optimum optical path length, so that measurement of the concentration of some other component may be rendered impossible. Therefore, for the purpose of carrying out concentration measurement with respect to a plurality of components which require different optimum optical path lengths, it is desirable to simultaneously use both the integrating sphere for measuring the quantity of transmitted light and the integrating sphere for measuring the quantity of reflected light.

For the light receiving means, optical fiber or condenser lens may be used instead of the integrating sphere.

Figure 10:
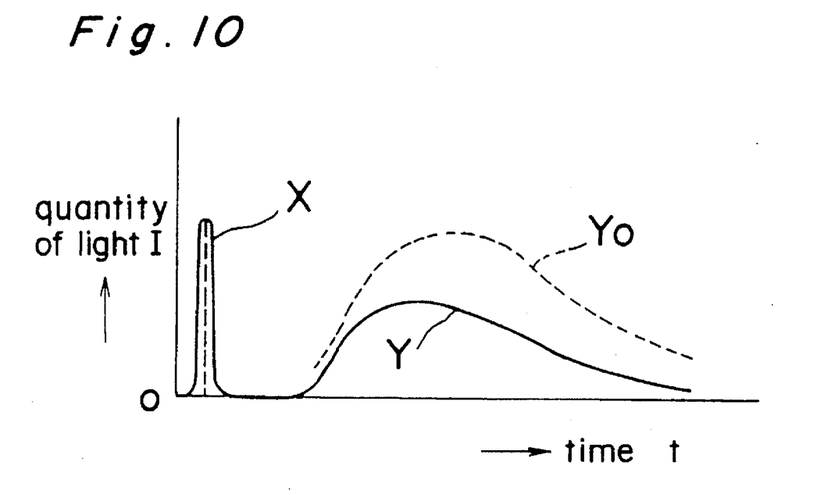
FIG. 10 is a chart showing the quantity of light of pulse laser of a single wavelength (curve X) generated from the light irradiator, the quantity of transmitted light from the object (curve Y), and the quantity of transmitted light from the object without light absorption (curve $Y_o$) in relation to lapse of time.

FIG. 10 shows the relationship between the quantity of pulse laser of a single wavelength (curve X) generated from the light irradiator 1 and also the quantity of transmitted light from the object 12 which is detected by the integrating sphere 18 (curve Y), on one hand, and lapse of time t, on the other.

Figure 11:
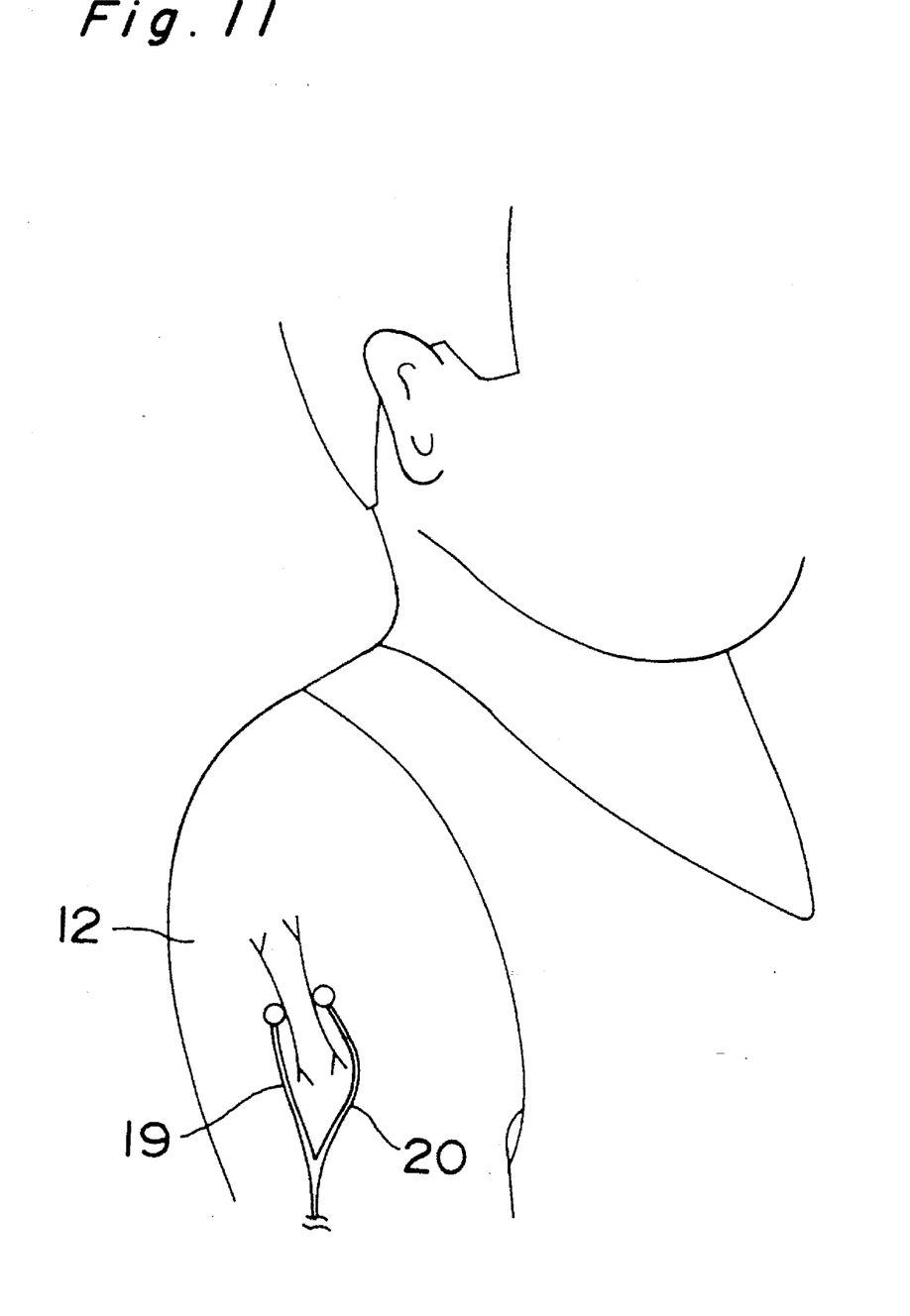
FIG. 11 is a schematic diagram showing an apparatus for measuring concentrations of components according to a sixth embodiment of one aspect of the present invention, to which methods for measuring concentrations of components of another aspect of the present invention are applied.

FIG. 11 shows an apparatus for measuring concentrations of components according to sixth embodiment of one aspect of the present invention, to which methods for measuring concentrations of components defined in claims 4 and 5 of another aspect of the present invention are applied. Parts identical with those of the foregoing embodiments are designated by like reference numerals, description being omitted with respect to those parts.

In this embodiment, the illuminating unit comprises a variable wavelength laser generating unit not shown, and an optical fiber element 19, for example, which conducts the laser from the variable wavelength laser generating unit to any desired site; and the photodetector comprises an optical fiber element 20 for conducting light made incident on any desired spot to the quantity of light sensing means not shown.

As shown, the arrangement is such that a part of a human body, for example, is pinched and the respective ends of the optical fiber elements 19, 20 are arranged on both sides of the pinched part in opposed relation, so that the concentration of a component, e.g., saccharide, of the human body or the object 12 can be measured in the same way as in the foregoing examples.

In the present invention, the light source in the illuminating unit 1 is not limited to the variable wavelength pulse laser 11, and needless to say, any light source capable of generating pulse light of different wavelengths may be conveniently employed.

As is apparent from the foregoing description, the invention comprises a light irradiator for projecting pulse light including different wavelengths toward an object, a photodetector for performing a time resolved measurement of the quantity of light with respect to at least one of reflected light and transmitted light from the object which is subject to changes with lapse of time after the generation of the pulse light, and an arithmetic unit for calculating concentrations of components in the object and outputting the calculation result such that the relationship between time lapse and measured quantity of light is converted into a relationship between an optical path length representing the distance of light travel within the object and a change in the measured quantity of light relative to a change in unit concentration so that the optical path length and the quantity of light which is measured when the change in the quantity of light is at a peak are stored in memory to enable selection of an optimum optical path length for each wavelength, with the quantity of light for the optimum optical path length being used as a basis for the calculation.

This makes it possible to calculate the concentration of a component from the quantity of reflected light or the quantity of transmitted light, both of them, at an optimum optical path length and an optimum wavelength which provide a maximum S/N ratio, in a non-destructive, non-invasive, and bloodless manner. Thus, it is possible to measure the concentration of the component within the object irrespective of the degree of concentration with respect to the component present in the object.

In its another aspect, the invention provides a method which comprises projecting pulse light of a selected wavelength from a light irradiator toward an object; causing a photodetector to perform a time resolved measurement of the quantity of light with respect to at least one of reflected light and transmitted light from the object which is subject to changes with lapse of time after the generation of the pulse light; storing the measured data in an arithmetic unit; and repeating the foregoing steps for different wavelengths of pulse light in such a manner that the arithmetic unit converts the relationship between time lapse and measured quantity of light into a relationship between an optical path length representing the distance of light travel within the object and a change in the measured quantity of light relative to the change in unit concentration so that the optical path length and the quantity of light which is measured when the change in the quantity of light is at a peak are stored in memory for each wavelength to enable selection of an optimum optical path length for each wavelength, whereby the concentrations of the components in the object is calculated on the basis of the quantity of light for the optimum optical path length, the calculated result being then out$_p$ut.

In a further aspect of the invention, there is provided a method which comprises the steps of:

(i) generating pulse light of a selected wavelength from a light irradiator and causing a photodetector to perform a time resolved measurement of the quantity of received light $I_R$ from an object which serves as a reference and is subject to changes with lapse of time t;

(ii) projecting pulse light of the selected wavelength from the light irradiator toward the object and causing the photodetector to perform a time resolved measurement of the quantity of transmitted light $I_t$ from the object which is subject to changes with lapse of time t;

(iii) with respect to the measured quantity of received light $I_R(L)$ and measured quantity of transmitted light $I_t(L)$ which are subject to changes with an optical path length L corresponding to lapse of time t, selecting a reference quantity of received light $I_R(L_o)$ and a reference quantity of transmitted light $I_t(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation $L=Ct$ which expresses the relationship between optical path length L and lapse of time t;

(vii) calculating the quantity of transmitted light $I_{tp}(t_p)$ from the object for a certain wavelength $\lambda$ at optimum lapse of time $t_p$;

(viii) calculating, on the basis of the quantity of received light $I_{RP}$ and quantity of transmitted light $I_{tp}$ at the optimum lapse of time and from equation $A=\log_{10}(I_R/I_t)$ for absorbance A, an absorbance $A_p$ corresponding to $I_{RP}$ and $I_{tp}$; and (ix) repeating the foregoing steps for plural wavelengths, whereby on the basis of respective calculated absorbances are carried out multivariate analysis to calculate the concentrations of the components in the object, the calculated results being then output.

The invention, in a still further aspect, provides a method which comprises the steps of:

(i) generating pulse light of a selected wavelength from a light irradiator and causing a photodetector to perform a time resolved measurement of the quantity of received light $I_R$ from an object which serves as a reference and is subject to changes with lapse of time t;

(ii) projecting pulse light of the selected wavelength from the light irradiator toward the object and causing the photodetector to perform a time resolved measurement of the quantity of reflected light $I_r$ from the object which is subject to changes with lapse of time t;

(iii) with respect to the measured quantity of received light $I_R(L)$ and measured quantity of reflected light $I_r(L)$ which are subject to changes with an optical path length L corresponding to lapse of time t, selecting a reference quantity of received light $I_R(L_o)$ and a reference quantity of reflected light $I_r(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation $L=Ct$ which expresses the relationship between optical path length L and lapse of time t;

(vii) calculating the quantity of reflected light $I_{rp}(t_p)$ from the object for a certain wavelength $\lambda$ at optimum lapse of time $t_p$;

(viii) calculating, on the basis of the quantity of received light $I_{RP}$ and quantity of reflected light $I_{rp}$ at the optimum lapse of time and from equation $A=\log_{10}(I_R/I_r)$ for absorbance A, an absorbance $A_p$ corresponding to $I_{RP}$ and $I_{rp}$; and (ix) repeating the foregoing steps for plural wavelengths, whereby on the basis of respective calculated absorbances are carried out multivariate analysis to calculate the concentrations of the components in the object, the calculated results being then output.

In another aspect, the invention provides a method which comprises the steps of:

(i) generating pulse light of a selected wavelength from a light irradiator and causing a photodetector to perform a time resolved measurement of the quantity of received light $I_R$ from an object which serves as a reference and is subject to changes with lapse of time t;

(ii) projecting pulse light of the selected wavelength from the light irradiator toward the object and causing the photodetector to perform a time resolved measurement of the quantity of transmitted light $I_t$ and quantity of reflected light $I_r$ from the object which are subject to changes with lapse of time t;

(iii) with respect to the measured quantity of received light $I_R(L)$, measured quantity of transmitted light $I_t(L)$ and measured quantity of reflected light $I_r(L)$ which are subject to changes with an optical path length L corresponding to lapse of time t, selecting a reference quantity of received light $I_R(L_o)$, a reference quantity of transmitted light $I_t(L_o)$, and a reference quantity of reflected light $I_r(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation $L=Ct$ which expresses the relationship between optical path length L and lapse of time t;

(vii) calculating the quantity of transmitted light $I_{tp}(t_p)$ and quantity of reflected light $I_{rp}(t_p)$ from the object for a certain wavelength $\lambda$ at optimum lapse of time $t_p$;

(viii) calculating, on the basis of the quantity of received light $I_{RP}$, quantity of transmitted light $I_{tp}$, and quantity of reflected light $I_{rp}$ at the optimum lapse of time and from equation $A=\log_{10}(I_R/I_r)$ for absorbance A, an absorbance $A_p$ corresponding to $I_{RP}$, $I_{tp}$ and $I_{rp}$; and (ix) repeating the foregoing steps for plural wavelengths, whereby on the basis of respective calculated absorbances are carried out multivariate analysis to calculate the concentrations of the components in the object, the calculated results being then output.

Thus, it is possible to calculate the concentration of the component from at least one of the quantity of reflected light and the quantity of transmitted light at an optimum optical path length which can provide a maximum S/N ratio in a non-destructive, non-invasive, and bloodless manner and, therefore, to measure the concentration of the component in the object with high accuracy and without regard to the degree of concentration of the component.

Although the present invention has been fully described by way of example with reference to the accompanying drawings, it is to be noted here that various changes and modifications will be apparent to those skilled in the art. Therefore, unless otherwise such changes and modifications depart from the scope of the present invention as defined by the appended claims, they should be construed as included therein.

What is claimed is:

1. An apparatus for measuring concentrations of components comprising a light irradiator for projecting pulse light of different wavelengths toward an object, a photodetector for performing a time resolved measurement of the quantity of light with respect to at least one of reflected light and transmitted light from the object which is subject to changes with lapse of time after the generation of the pulse light, and an arithmetic unit for calculating a component concentration in the object and outputting the calculation result such that the relationship between time lapse and measured quantity of light is converted into a relationship between an optical path length representing the distance of light travel within the object and a change in the measured quantity of light relative to a change in unit concentration so that the optical path length and the quantity of light which is measured when the change in the quantity of light is at a peak are stored in memory to enable selection of an optimum optical path length for each wavelength, with the quantity of light for the optimum optical path length being used as a basis for the calculation.

2. An apparatus for measuring concentrations of components as set forth in claim 1, wherein the illuminating unit comprises a laser generating unit capable of generating pulse laser of different wavelengths.

3. An apparatus for measuring concentrations of components as set forth in claim 2, wherein the laser generating unit is a variable wavelength laser generating unit.

4. A method for measuring concentrations of components which comprises projecting pulse light of a selected wavelength from a light irradiator toward an object; causing a photodetector to perform a time resolved measurement of the quantity of light with respect to at least one of reflected light and transmitted light from the object which is subject to changes with lapse of time after the generation of the pulse light; storing the measured data in an arithmetic unit; and repeating the foregoing steps for different wavelengths of pulse light in such a manner that the arithmetic unit converts the relationship between time lapse and measured quantity of light into a relationship between an optical path length representing the distance of light travel within the object and a change in the measured quantity of light relative to the change in unit concentration so that the optical path length and the quantity of light which is measured when the change in the quantity of light is at a peak are stored in memory for each wavelength to enable selection of an optimum optical path length for each wavelength, whereby concentrations of components in the object is calculated on the basis of the quantity of light for the optimum optical path length, the calculated result being then output.

5. A method for measuring concentrations of components which comprises the steps of:

(i) generating pulse light of a selected wavelength from a light irradiator and causing a photodetector to perform a time resolved measurement of the quantity of received light $I_R$ from an object which serves as a reference and is subject to changes with lapse of time t;

(ii) projecting pulse light of the selected wavelength from the light irradiator toward the object and causing the photodetector to perform a time resolved measurement of the quantity of transmitted light $I_t$ from the object which is subject to changes with lapse of time t;

(iii) with respect to the measured quantity of received light $I_R(L)$ and measured quantity of transmitted light $I_t(L)$ which are subject to changes with an optical path length L corresponding to lapse of time t, selecting a reference quantity of received light $I_R(L_o)$ and a reference quantity of transmitted light $I_t(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation $L=Ct$ which expresses the relationship between optical path length L and lapse of time t;

(vii) calculating the quantity of transmitted light $I_{tp}(t_p)$ from the object for a certain wavelength $\lambda$ at optimum lapse of time $t_p$;

(viii) calculating, on the basis of the quantity of received light $I_{RP}$ and quantity of transmitted light $I_{tp}$ at the optimum lapse of time and from equation $A=\log_{10}(I_R/I_t)$ for absorbance A, an absorbance $A_p$ corresponding to $I_{RP}$ and $I_{tp}$; and (ix) repeating the foregoing steps for plural wavelengths, whereby on the basis of respective calculated absorbances are carried out multivariate analyses to calculate the concentrations of the components in the object, the calculated results being then output.

6. A method for measuring concentrations of components which comprises the steps of:

(i) generating pulse light of a selected wavelength from a light irradiator and causing a photodetector to perform a time resolved measurement of the quantity of received light $I_R$ from an object which serves as a reference and is subject to changes with lapse of time t;

(ii) projecting pulse light of the selected wavelength from the light irradiator toward the object and causing the photodetector to perform a time resolved measurement of the quantity of reflected light $I_r$ from the object which is subject to changes with lapse of time t;

(iii) with respect to the measured quantity of received light $I_R(L)$ and measured quantity of reflected light $I_r(L)$ which are subject to changes with an optical path length L corresponding to lapse of time t, selecting a reference quantity of received light $I_R(L_o)$ and a reference quantity of reflected light $I_r(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation L=Ct which expresses the relationship between optical path length L and lapse of time t;

(vii) calculating the quantity of reflected light $I_{rp}(t_p)$ from the object for a certain wavelength $\lambda$ at optimum lapse of time $t_p$;

(viii) calculating, on the basis of the quantity of received light $I_{RP}$ and quantity of reflected light $I_{rp}$ at the optimum lapse of time and from equation $A=\log_{10}(I_R/I_r)$ for absorbance A, an absorbance $A_p$ corresponding to $I_{RP}$ and $I_{rp}$; and (ix) repeating the foregoing steps for plural wavelengths, whereby on the basis of respective calculated absorbances are carried out multivariate analyses to calculate the concentrations of the components in the object, the calculated results being then output.

7. A method for measuring concentrations of components which comprises the steps of:

(i) generating pulse light of a selected wavelength from a light irradiator and causing a photodetector to perform a time resolved measurement of the quantity of received light $I_R$ from an object which serves as a reference and is subject to changes with lapse of time t;

(ii) projecting pulse light of the selected wavelength from the light irradiator toward the object and causing the photodetector to perform a time resolved measurement of the quantity of transmitted light $I_t$ and quantity of reflected light $I_r$ from the object which are subject to changes with lapse of time t;

(iii) with respect to the measured quantity of received light $I_R(L)$, measured quantity of transmitted light $I_t(L)$ and measured quantity of reflected light $I_r(L)$ which are subject to changes with an optical path length L corresponding to lapse of time t, selecting a reference quantity of received light $I_R(L_o)$, a reference quantity of transmitted light $I_t(L_o)$, and a reference quantity of reflected light $I_r(L_o)$ at a reference optical path length $L_o$ corresponding to a certain reference lapse of time $t_o$;

(iv) calculating value $\gamma_o$ for $\gamma$ at reference optical path length $L_o$ from equation $I_t(L)=I_R(L)t\gamma$ (where, t: transmittance of light relative to the object);

(v) calculating optical path length ratio $k_p$ corresponding to an optical path length $L_p$ which gives a maximum sensitivity for quantity-of-light measurement, from an equation $k=-1/\log_{10}\gamma_o$ which expresses the relationship between optical path length ratio $k=L/L_o$ and $\gamma_o$ at reference optical path length $L_o$;

(vi) calculating an optimum lapse of time $t_p$ corresponding to the optimum optical path length $L_p$ from equation L=Ct which expresses the relationship between optical path length L and lapse of time t;

(vii) calculating the quantity of transmitted light $I_{tp}(t_p)$ and quantity of reflected light $I_{rp}(t_p)$ from the object for a certain wavelength $\lambda$ at optimum lapse of time $t_p$;

(viii) calculating, on the basis of the quantity of received light $I_{RP}$, quantity of transmitted light $I_{tp}$, and quantity of reflected light $I_{rp}$ at the optimum lapse of time and from equation $A=\log_{10}(I_R/I_r)$ for absorbance A, an absorbance $A_p$ corresponding to $I_{RP}$, $I_{tp}$ and $I_{rp}$; and (ix) repeating the foregoing steps for plural wavelengths, whereby on the basis of respective calculated absorbances are carried out multivariate analyses to calculate the concentrations of the components in the object, the calculated results being then output.

* * * * *